(12) United States Patent
Cao

(10) Patent No.: US 11,896,729 B2
(45) Date of Patent: Feb. 13, 2024

(54) UV DISINFECTION SYSTEM

(71) Applicant: CAO Group, Inc., West Jordan, UT (US)

(72) Inventor: Densen Cao, Sandy, UT (US)

(73) Assignee: CAO Group, Inc., West Jordan, UT (US)

( * ) Notice: Subject to any disclaimer, the term of this patent is extended or adjusted under 35 U.S.C. 154(b) by 0 days.

(21) Appl. No.: 18/000,262

(22) PCT Filed: May 28, 2021

(86) PCT No.: PCT/US2021/035003
§ 371 (c)(1),
(2) Date: Nov. 29, 2022

(87) PCT Pub. No.: WO2021/247442
PCT Pub. Date: Dec. 9, 2021

(65) Prior Publication Data
US 2023/0241264 A1    Aug. 3, 2023

Related U.S. Application Data

(60) Provisional application No. 63/033,044, filed on Jun. 1, 2020.

(51) Int. Cl.
A61L 2/10    (2006.01)

(52) U.S. Cl.
CPC ........... A61L 2/10 (2013.01); *A61L 2202/122* (2013.01); *A61L 2202/14* (2013.01)

(58) Field of Classification Search
CPC ... A61L 2/10; A61L 2202/122; A61L 2202/14
USPC ........................... 250/453.11, 454.11, 455.11
See application file for complete search history.

(56) References Cited

U.S. PATENT DOCUMENTS

| | | | |
|---|---|---|---|
| 6,303,086 B1 * | 10/2001 | Heimer | C02F 1/325 422/186.3 |
| 6,877,248 B1 | 4/2005 | Cross et al. | |
| 2003/0034459 A1 | 2/2003 | Bonin | |
| 2006/0221330 A1 | 10/2006 | Waldo et al. | |
| 2009/0147523 A1 * | 6/2009 | Levon | F21V 7/00 362/350 |
| 2010/0213392 A1 * | 8/2010 | Hatzav | F21V 33/0032 250/492.1 |
| 2011/0162226 A1 | 7/2011 | Witt | |

* cited by examiner

*Primary Examiner* — Nicole M Ippolito
(74) *Attorney, Agent, or Firm* — Dobbin IP Law, P.C.; Geoffrey E. Dobbin

(57) ABSTRACT

An UV disinfection system (200) may feature a chamber (207) with internal spherical reflective surfaces (208) to evenly reflect UV radiation from all angles to direct the UV radiation to all surface area of the object inside the chamber to disinfect object utilizing UV radiation under controlled time. An object (215) to be disinfected may reside within the chamber (207) on a UV transparent rack or shelf (214). The spherical reflective surfaces may be fashioned by placing such surfaces on a polyhedral internal structure or making the internal chamber spherical in and of itself (208). Multiple UV sources (209*a*), (209*b*) may also be utilized.

9 Claims, 3 Drawing Sheets

UV DISINFECTION SYSTEM

CROSS-REFERENCES TO RELATED APPLICATIONS

This application claims priority to prior filed U.S. Application No. 63/033,044, filed Jun. 1, 2020, and incorporates the same by reference in its entirety.

FIELD OF THE INVENTION

The present invention relates to the field of equipment disinfection and more particularly relates to a chamber for disinfection which utilizes ultraviolet electromagnetic radiation to perform disinfection operations.

BACKGROUND OF THE INVENTION

Ultraviolet (UV) radiation can be used for many applications including, but not limited to, disinfection, material curing, and communications. Ultraviolet radiation is typically classified in three bands: UVA referring wavelength from 315 to 400 nm, UVB referring wavelength from 280 to 315 nm, and UVC referring wavelengths from 100 to 280 nm. The UVC band has been known to effectively kill bacteria and viruses on contaminated surfaces when those surfaces are exposed to UV light at a critical energy level. The use of UV radiation for disinfection has been demonstrated in water purification, air purification, and surface disinfection with different physical formats. UV disinfection has many advantages over traditional disinfection methods such as the use of heat, pressure, steam, and/or liquids. Disinfection by UV radiation can be done in a few seconds with sufficient UV radiation energy. The traditional disinfection methods take much longer time and have additional processes. However, one of challenges of using UV light for disinfection is to have light with sufficient energy density striking every surface of and location on objects desired to be disinfected. Also, UV light is naturally harmful to skin and eyes, so safety measures for using UV light are also needed.

This invention describes a system enable UVC light to reach all locations and surfaces about an object requiring disinfection. The present invention utilizes a UVC transparent rack and spherical reflectors inside of a UV disinfection chamber to allow uniform distribution of UV energy to strike all exposed surfaces of the object desired to be disinfected. The present invention represents a departure from the prior art in that the system of the present invention allows for uniform saturation of an object's surfaces with UVC radiation.

SUMMARY OF THE INVENTION

In view of the foregoing disadvantages inherent in the known types of disinfection chambers, an improved UV disinfection system may provide a chamber that meets at least the following objectives: it effectively transmits UV radiation of sufficient energy density to perform disinfection, that the UV radiation be transmitted to every exposed surface of the object to be disinfected, that it be simple to operate, and that it be economical to manufacture. As such, a new and improved UV disinfection system may comprise at least one UV light source and at least one UV transparent support surface situated in a chamber with spherical reflectors, either the chamber itself may be spherical or may contain a plurality of reflectors to accomplish these objectives.

The more important features of the invention have thus been outlined in order that the more detailed description that follows may be better understood and in order that the present contribution to the art may better be appreciated. Additional features of the invention will be described hereinafter and will form the subject matter of the claims that follow.

Many objects of this invention will appear from the following description and appended claims, reference being made to the accompanying drawings forming a part of this specification wherein like reference characters designate corresponding parts in the several views.

Before explaining at least one embodiment of the invention in detail, it is to be understood that the invention is not limited in its application to the details of construction and the arrangements of the components set forth in the following description or illustrated in the drawings. The invention is capable of other embodiments and of being practiced and carried out in various ways. Also, it is to be understood that the phraseology and terminology employed herein are for description and should not be regarded as limiting.

As such, those skilled in the art will appreciate that the conception, upon which this disclosure is based, may readily be utilized as a basis for the designing of other structures, methods, and systems for carrying out the several purposes of the present invention. It is important, therefore, that the claims be regarded as including such equivalent constructions insofar as they do not depart from the spirit and scope of the present invention.

DETAILED DESCRIPTION OF THE PREFERRED EMBODIMENT

With reference now to the drawings, a preferred embodiment of the UV disinfection chamber is herein described. It should be noted that the articles "a", "an", and "the", as used in this specification, include plural referents unless the content clearly dictates otherwise.

Figure 1:
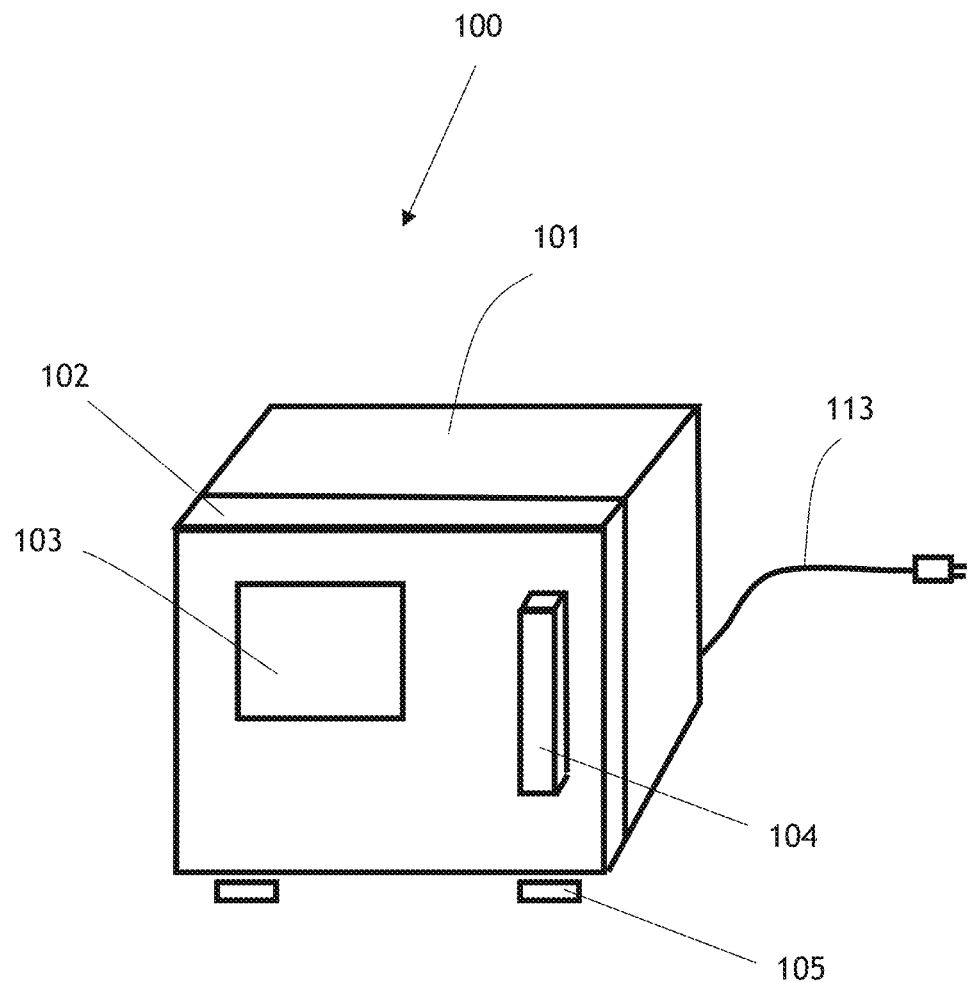
FIG. 1 is a schematic detailing the exterior of a UV disinfection chamber to be utilized with the system.

With reference to FIG. 1, an UV disinfection system (100) comprises a casing (101), a door (102), a display for system information (103), and a door handle (104) to open and lock the door, accessing an inner chamber. Footings (105) may be provided to add surface stability to the system (100), and a power cord (113) may be used to connect to electrical power. The system can also be powered by a battery if needed.

Figure 2:
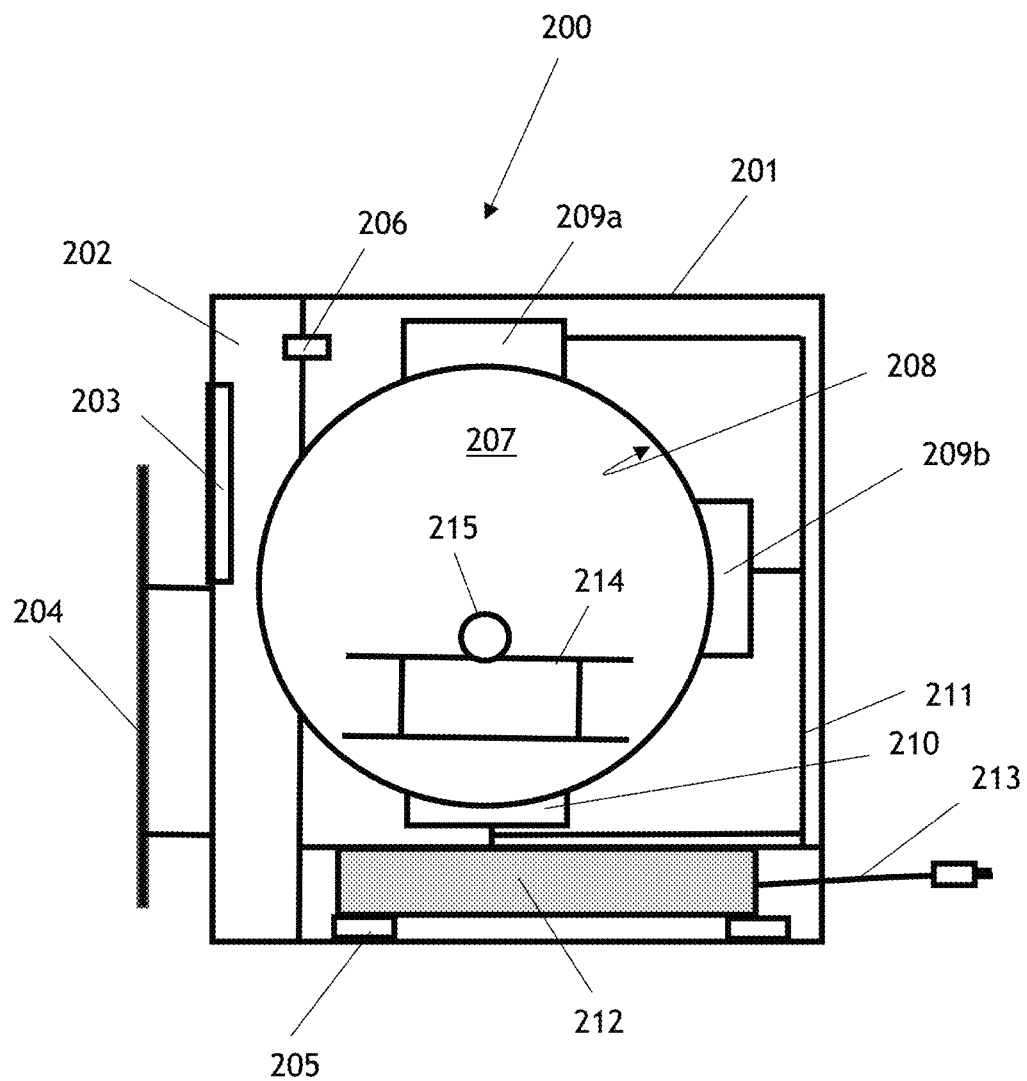
FIG. 2 is a schematic of one embodiment of the inside of a chamber, such as depicted in FIG. 1.

FIG. 2 depicts a schematic profile of one embodiment of an UV disinfection chamber where (200) is the system. As illustrated before, a casing (201) with a door (202), handle (204), footings (205), and system display (203) are provided. The system display (203) may provide the user control interface for the disinfection chamber. Power supply (213) is also provided. A door interlock (206) is also provided. When the interlock (206) is triggered by opening the door, it will shut off all UV light in the system to prevent accidental UV emission, harming the user. Securing the interlock (206) is a prerequisite to UV light emission and is a failsafe switch for the safety of the user.

The preferred chamber (207) is the key component of the invention. The inner profile of chamber (207) is a predominantly a hollow sphere (possibly, but not necessarily, excepting the inner door surface) with an inner sphere surface (208). The surface (208) will be highly reflective to the light source, particularly for UVC wavelengths. Surface (208) may be coated with a reflective paint, a reflective film, or may be an uncoated, polished, or mirrored machined surface. Two UVC light sources (209a), (209b) are positioned in different locations of the chamber (207). The light sources (209a), (209b) can be LEDs or any other type of light producing structure that may produce the desired wavelength and power. The light sources (209a), (209b) can each be a single source or a plurality of smaller sources depending on the needs for light intensity. The UVC light source can be one or more LEDs, mercury lamps or any other sources suitable for the emission of UVC light. Likewise, there may be more than two sources, or even only one source (though this would in some ways limit the inventions effectiveness). The beam angle of any light source can be ranged from 0.1 to 360 degrees. A power sensor (210) is provided to measure the power inside the chamber to ensure that the light power is always meeting requirements for the intended operation. There are wire connections (211) to connect light sources (209a), (209b) to a control circuit (212) which is connected to a power source (206). The control circuit (212) along with system display panel (203) and user control interface on the door are used to control the disinfection time and other conditions, as determined by the user. The disinfection time for objects depends on the total available UV energy into the chamber. The power source for the unit can be wall plug or battery. Inside the chamber (207), a rack (214) may be used to hold the object (215) intended to be disinfected. The material of rack shall be UVC transparent and may be made of glasses, quartz, plastic, or polymers.

The working principle is that when the light sources (209a), (209b) emit UVC radiation with sufficient energy density into chamber (207) with its highly reflective surface (208). Then, the light radiation will be reflected infinitely inside the chamber and will reach to every single location inside the chamber (207) so that an object (215) inside the chamber will have every exposed surface struck by the light from every angle and the light will not be hindered by the transparent rack (214). For purposes of this Application, defining the inner chamber (207) as "spherical" may exclude the inner surface of the door (202) as a part of the "spherical" surface and would include any shape that is generally concave in relation to its interior, including any ovoid or paraboloid chamber that is not perfectly spherical.

Figure 3:
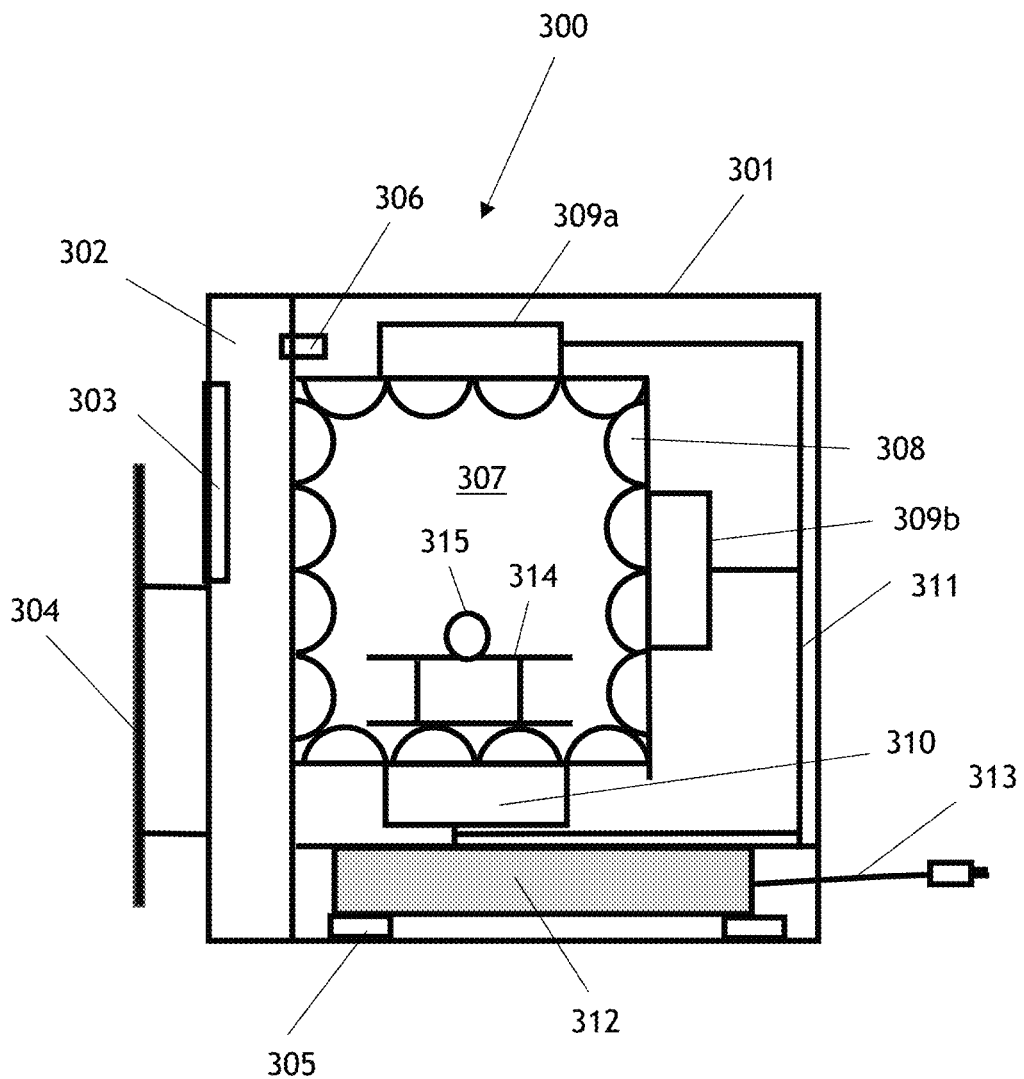
FIG. 3 is a schematic of an alternate embodiment of the inside of a chamber, such as depicted in FIG. 1.

FIG. 3 depicts a profile of a second embodiment of a UV disinfection chamber (300), where (301) is casing with footing (305), (302) is the door to access inside of chamber (307) and handle (304) is provided. A display for system information and user control (303) is also provided. A door interlock (306) of similar principals as described in the first embodiment (200) is also provided. In this second embodiment, the inner profile of chamber (307) is a cubic or other polyhedral shape with at least one semisphere, or other partial sphere, (308) mounted upon the internal face of the chamber (307) thereby creating at least one convex reflector. The surface of each semisphere (308) will be highly reflective to the light source, particularly for UVC wavelengths and, like the spherical surface of the first embodiment, may be coated with reflective paint, reflective film, or have a reflective but uncoated, polished, or mirrored machined surface. At least two UVC light sources (309a), (309b) are positioned in different location of the chamber (307) along the same principles, properties, and capabilities as described before. A light power sensor (310) is used to measure the light intensity inside the chamber to ensure that the light intensity will meet the requirements. Wire connections (311) to connect light sources (309a), (309b) to a control circuit (312) which is connected to a power source (313). As with the prior embodiment, the control circuit (312) and display panel (303) on the door are used to control the disinfection time and other conditions. The disinfection time for objects depends on the total available UV energy into the chamber. The power source can be wall plug or battery. Like the first embodiment, an object (315) is held on a UVC transparent rack (314) made of glass, quartz, plastic, or other polymers inside the chamber (307). When the light sources (309a), (309b) emit UV radiation of sufficient energy density into the polyhedral chamber (307), with multiple semispheres (308) on each face, the light will be reflected infinitely inside the chamber (307) and will reach to every single location inside the chamber (307), striking the object (315) on every exposed surface of the object. For purposed of this Application, the term "polyhedral" shall include any volume defined at least in part by flat sides, even if one or more sides are rounded.

INDUSTRIAL APPLICABILITY

The invention has relevance in the field of disinfection, particularly in the medical and dental fields in relation to the disinfection of tools and other objects of use. The invention may also be made as a product of industry. Although the present invention has been described with reference to preferred embodiments, numerous modifications and variations can be made and still the result will come within the scope of the invention. No limitation with respect to the specific embodiments disclosed herein is intended or should be inferred.

What is claimed is:
1. A disinfecting system comprising:
   a housing defining a polyhedral internal chamber, defined by a plurality of internal faces, with an internal surface, said internal surface further comprising at least one reflective spherical component, said at least one reflective spherical component further comprising at least one semi-spherical reflector positioned on each internal face;
   at least one source of UV radiation configured to emit UV radiation into the internal chamber;
   wherein the UV radiation is reflected off the internal surface of the internal chamber in a manner to strike all exposed surfaces of an object contained within the internal chamber.

2. The disinfecting system of claim 1, the spherical component of internal chamber being that the internal chamber itself is spherical.

3. The disinfecting system of claim 1, further comprising a light power sensor to detect light intensity.

4. The disinfection system of claim 1, further comprising a light transparent rack within the internal chamber to hold the objects intended to be disinfected.

5. The disinfection system of claim 1, the source of UV radiation being selected from the set of UV emission sources consisting of: at least one LED or at least one Mercury lamp.

6. The disinfection system of claim 1, further comprising a display to show system operating status.

7. The disinfection system of claim 1, further comprising a door to provide access into the internal chamber.

8. The disinfection system of claim 1, further comprising a door interlock system operably connected to the at least one source of UV radiation such that activation of the door interlock system is accomplished when the door is closed, and such activation is required to activate the at least one source of UV radiation.

9. The disinfection system of claim 1, further comprising a control system to control the emitted UV radiation and disinfection time.

\* \* \* \* \*